US00PP08777P

United States Patent [19]

Austin

[11] Patent Number: Plant 8,777

[45] Date of Patent: Jun. 14, 1994

[54] ROSE PLANT AUSCOUNTRY

[75] Inventor: David C. H. Austin, Wolverhampton, England

[73] Assignee: David Austin Roses Limited, Wolverhampton, England

[21] Appl. No.: 26,461

[22] Filed: Apr. 23, 1993

[51] Int. Cl.[5] ..... A01H 5/00

[52] U.S. Cl. ..... Plt./1

[58] Field of Search ..... Plt. 1

*Primary Examiner*—James R. Feyrer

*Attorney, Agent, or Firm*—Klarquist, Sparkman, Campbell, Leigh & Whinston

[57] ABSTRACT

A shrub *Rosa hybrida* rose plant is disclosed having old-fashioned-style pale pink flowers with green centers, and repeat flowering.

1 Drawing Sheet

The present invention relates to a new and distinct variety of rose plant of the shrub class which was originated by me by crossing the variety "Wife of Bath" with the variety "Graham Thomas". The variety "Wife of Bath" (unpatented) has cup-shaped flowers of a slightly darker pink than AUSCOUNTRY and has rather weak growth. "Graham Thomas" (unpatented) has golden-yellow, cup-shaped flowers and possesses vigorous, bushy growth.

The primary objective of this breeding was to produce a new rose variety having the repeat flowering of its parents with olf-fashioned-type flowers. The objective was substantially achieved along with other desirable improvements as evidenced by the following unique combination of characteristics which are outstanding in the new variety and which distinguish it from its parents, as well as from all other varieties of which I am aware:

1. Old-fashioned-style flowers having pale pink color and green centers resulting from enlarged green-colored styles that extend above the small petals in the middle of the flowers; and 2. Repeat flowering.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new vareity in different stages of development, depicted in color as nearly true as it is reasonably possible to make the same in a color illustration of this character.

The following is a detailed description of my new rose cultivar with color descriptions using terminology in accordance with The Royal Horticultural Society (London) Color Chart, except where ordinary dictionary significance of color is indicated.

Parentage:

*Seed parent.*—"Wife of Bath" variety.

*Pollen parent.*—"Graham Thomas" variety.

Classification:

*Botanical.*—*Rosa hybrida.*

*Commercial.*—Shrub.

FLOWER

Observations made from specimens grown in a garden environment in Albrighton, Wolverhampton, England, in August, 1992.

Blooming habit: Recurrent.

Bud:

*Size.*—2.5 to 4 cm, when the petals start to unfurl.

*Form.*—Short, pointed ovoid.

*Color.*—When sepals first divide, bud color is Red-Purple Group 61C. When half blown, the upper sides of the petals are Red-Purple Group 73C; and the lower sides of the petals are Red-Purple Group 73D.

*Sepals.*—Color: Green Group 144A/B. Surface texture: Glandular. There are three heavily appendaged sepals. There are two unappendaged sepals with hairy edges.

*Receptacle.*—Color: Green Group 144B. Shape: Funnel. Size: Medium (about 5–6 mm×7–8 mm), slender. Surface: Smooth or slightly glandular.

*Peduncle.*—Length: Averaging about 5–7 cm. Surface: Glandular. Color: Medium green. Strength: Erect.

Bloom:

*Size.*—Medium. Average open size is 7.5 cm.

*Borne.*—Singly and several together, in clusters having irregular shape.

*Stems.*—Medium length, normal strength. Average length is about 70–90 cm.

*Form.*—When first open: Cupped. Permanence: Flattens, outer petal edges curl slightly.

*Petalage.*—Number of petals under normal conditions: 130. Range: 110 to 140.

*Petal size.*—From 15 mm×15 mm to 45 mm long×40 mm wide.

*Color.*—The upper side of the petals is Red-Purple Group 62D. The reverse side of the petals is Red-Purple Group 65D. The base of petals is Yellow-Orange Group 19D. The major color on the upper side is Red Group 36C.

*Variegations.*—None.

*Discoloration.*—The general tonality at the end of the first day is slightly paler. At the end of the third day: Slight paler, Red Group 36D.

*Fragrance.*—Moderate to strong. Fruity.

Petals:

*Texture.*—Medium thick.

*Shape.*—Round notched.

*Form.*—Tips slightly recurved.

*Arrangement.*—Quartered, with few, small petaloids in the center.

*Persistence.*—Petals drop off cleanly before drying.

*Lastingness.*—On the plant: About 5 days. As a cut flower: About 4 days.

Reproductive parts:

*Anthers.*—Size: Medium. Quantity: Few. Color: Yellow. Arrangement: Tucked in calyx or partly so, mixed with petaloids.

*Filaments.*—Color: Very pale yellow.

*Pollen.*—Color: Lemon yellow.

*Styles.*—Color: Green Group 144C.

*Stigmas.*—Color: Greenish white. Hips: Formed rarely.

Form: Shrub with much branching in upper part of plant.

Growth: Medium vigor.

*Size.*—Height: 105 cm. Width: 75 cm.

Foliage: Number of leaflets on normal mid-stem leaves: 5.

*Size.*—About 18–20 cm long × 15–16 cm wide.

*Quantity.*—Normal.

*Color.*—New foliage: Green Group 144D. Old foliage: Green Group 144D.

Leaflets:

*Shape.*—Pointed oval.

*Texture.*—Upper side: Smooth.

*Serration.*—Small double and single serrations.

*Petiole rachis.*—Color: Reddish.

*Petiole underside.*—With prickles.

*Stipules.*—About 2.5–3.0 cm long.

*Disease resistance.*—Resistant to mildew and blackspot under normal growing conditions at Albrighton, Wolverhampton, England.

Wood:

*New wood.*—Color: Light green. Bark: Smooth.

*Old wood.*—Color: Green. Bark: Smooth.

Prickles:

*Quantity.*—Ordinary number on main canes from base and on laterals from main canes.

*Form.*—Medium length, straight and slightly hooked downward.

*Color when young.*—Green.

*Position.*—Evenly spread.

Small prickles:

*Quantity.*—None on main stalks or on laterals.

I claim:

1. A new and distinct variety of *Rose hybrida* rose plant of the shrub class, substantially as herein shown and described, characterized particularly as to novelty by the unique combination of its old-fashioned-style pale pink flowers with green centers, and repeat flowering.

* * * * *

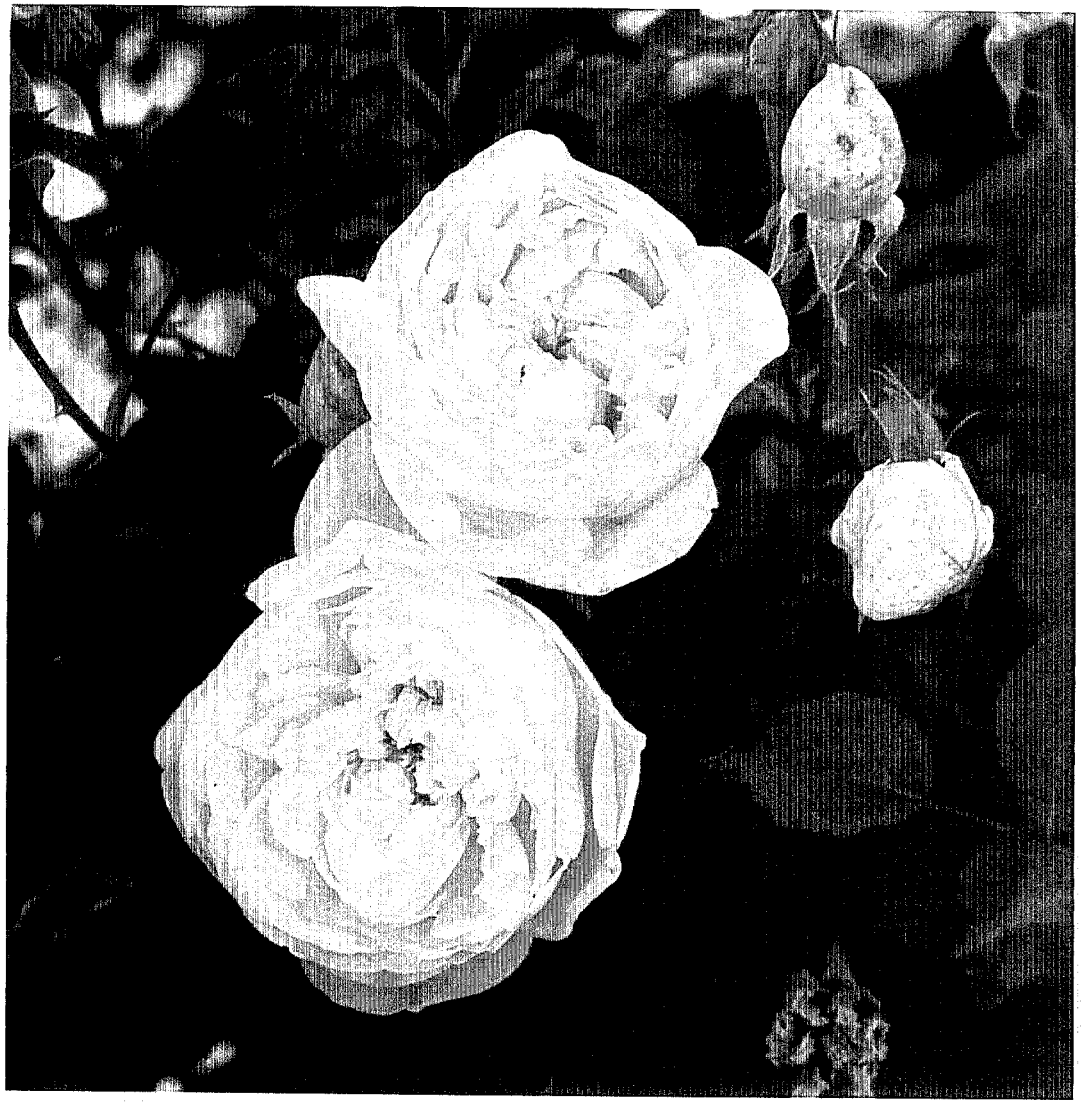

UNITED STATES PATENT AND TRADEMARK OFFICE

CERTIFICATE OF CORRECTION

PATENT NO. : PP 8,777

DATED : June 14, 1994

INVENTOR(S) : David Charles Henshaw Austin

It is certified that error appears in the above-identified patent and that said Letters Patent is hereby corrected as shown below:

Column 1, line 13, "olf-fashioned" should read --old-fashioned--.

Column 1, line 40, "Color" should read --Colour--.

Signed and Sealed this

Eleventh Day of October, 1994

Bruce Lehman

*Attest:*

BRUCE LEHMAN

*Attesting Officer*

*Commissioner of Patents and Trademarks*